United States Patent [19]

Wang

[11] Patent Number: 4,806,483
[45] Date of Patent: Feb. 21, 1989

[54] PROCESS FOR REGENERATING CORN

[75] Inventor: Andrew S. Wang, Palo Alto, Calif.

[73] Assignee: Sungene Technologies Corporation, San Jose, Calif.

[21] Appl. No.: 897,422

[22] Filed: Aug. 18, 1986

[51] Int. Cl.$^4$ .......................... C12N 5/00; C12N 5/02
[52] U.S. Cl. ............................ 435/240.49; 435/240.5; 435/240.51; 435/240.54
[58] Field of Search .............. 47/58; 435/240.1, 240.4, 435/240.45, 240.46, 240.42, 240.5, 240.51, 240.54, 240.49

[56] References Cited

PUBLICATIONS

Armstrong et al., (1985) Planta 164: 207-14.
Gingenbach (1977) Planta "Development of Maize Caryopses Resulting from in-vitro Pollination".
C. E. Green et al., Crop Science 14, 54 (1974).
M. Nesticky et al., Z. Pflanzenzuchtung 91, 322 (1983).
E. Lupotto, Annals of Botany 54, 523 (1984).
T. Abe et al., Theor. Appl. Genet. 72, 3 (1986).
P. Suprasanna et al., Theor. Appl. Genet. 72, 120 (1986).
G. M. Reddy, Abstract, Int. Cong. of Plant Tissue & Cell Cult., Aug. 1986.
C. T. Harms et al., Z. Pflanzenzuchtung 77, 347 (1976).
M. A. Santos et al., Plant Science Letters 33, 309 (1984).
Ahloowalia, Abstract, Int. Cong. of Plant Tissue & Cell Cult., Aug. 1986.
H. Wenzler et al., Protoplasma 131, 103 (1986).
Gupta et al., Abstract, Int. Cong. of Plant Tissue & Cell Cult., Aug. 1986.
Y. F. Chang, Plant Cell Reports 2, 183 (1983).
Y. C. Ting et al., Plant Science Letters 23, 139 (1981).
S. J. Molnar et al., Maize Genet. Corp. News Letter 54, 52 (1980).
J. M. Torne et al., Plant Science Letters 33, 317 (1984).
Pareddy et al., Plant Cell Tissue Organ Culture 5, 119 (1985).
King et al., in Handbook of Plant Cell Culture, vol. 1, Evans et al. Ed., MacMillian Publishing Co., New York, pp. 69-91 (1983).
Vasil, V. et al., in Cell Culture and Somatic Cell Genetics of Plants vol. 3, Vasil, I. K., Ed., Academic Press, Orlando, pp. 121-150 (1986).
Vasil, I. K. et al., in Cell Culture and Somatic Cell Genetics of Plants, vol. 3, Vasil, I. K. Ed., Academic Press, Orlando, pp. 121-150 (1986).

Primary Examiner—Charles F. Warren
Assistant Examiner—David T. Fox
Attorney, Agent, or Firm—Robbins & Laramie

[57] ABSTRACT

The invention is directed to a process for regenerating plants from mature corn embryos. The process comprises the steps of culturing the mature embryo on a callus induction medium to induce callus, subculturing the callus on a maintenance medium to maintain the callus, and subculturing the maintained callus on a regeneration medium to produce plants.

18 Claims, No Drawings

PROCESS FOR REGENERATING CORN

BACKGROUND OF THE INVENTION

1. Field of the Invention

The present invention relates to a process for regenerating corn from mature embryos of many varieties of corn.

2. Description of the Prior Art

Plant regeneration from cells in culture is essential for the application of somatic hybridization, for the production of new varieties through somaclonal variation and for the use of genetic engineering in producing new varieties. Although plants can be regenerated from tissue culture of several varieties of corn, there are many varieties for which this has not been accomplished using similar techniques.

In recent years, plant cell culture successes have had a considerable influence on the understanding of the respective roles of cell and organism in control of plant growth and development. Isolated plant cells have been shown to be amenable to in vitro culture and complete plants have been regenerated from cultures derived from somatic tissues, either directly via somatic embryogenesis or indirectly via organogenesis. Generally the regeneration pathway of choice is determined empirically by the manipulation of extrinsic factors, especially growth regulators. Early investigations of certain plant species have suggested that exogenous auxin concentration is a major factor controlling somatic embryogenesis, such that its reduction leads to the initiation of embryoid formation. In other species, exposure to a definite balance of auxin and cytokinin leads to the occurrence of organogenesis (shoots, then roots).

The process which has become the standard system for corn tissue culture is described by Green et al., *Crop Science* 15, 417 (1975). In this process, immature embryos were plated onto a callus induction medium which comprises the MS mineral salts, Straus vitamins and amino acids (glycine, asparagine, niacin, thiamine, pyridoxine and pantothenic acid), 2% sucrose, 0.8% agar and a hormone selected from 2,4-dichlorophenoxyacetic acid (2,4-D), p-chlorophenoxyacetic acid (PCA), alpha-naphthaleneacetic acid (NAA), 2-isopentyladenine (2-ip) or mixtures thereof. Plantlets were regenerated by subculturing the callus on medium containing reduced hormone concentrations. Hormone concentrations which were useful were 3 mg/l 2,4-D and a mixture of 1 mg/l 2,4-D, 4 mg/l NAA and 0.05 mg/l 2-ip. Regeneration was then accomplished on medium containing 0.25 mg/l 2,4-D or a mixture of 1 mg/l NAA and 0.05 mg/l 2-ip, respectively. All culturing was conducted in a 16 hour light/8 hour dark cycle for 3-4 week intervals before transfer. This reference reports that callus induction did not occur in one of five genotypes tested.

Similar results with different media have been demonstrated by Freeling et al., *Maydica* 21, 97 (1976); Vasil et al., *Theor. Appl. Genet.* 66, 285 (1983); Edallo et al., *Maydica* 26, 39 (1981); Lu et al., *Theor. Appl. Genet.* 62, 109 (1982); Hibberd et al., *Proc. Nat. Acad. Sci. USA* 74, 5113 (1977); and Green et al., *Crop Science* 14, 54 (1974). The latter reference also demonstrates genotype effects on callus induction.

Although this procedure has been unsuccessful for regenerating plants from all maize genotypes, the regeneration of most genotypes is now possible through the substitution of dicamba for 2,4-D in the media. See published European Patent Application No. 0 177 738 and Duncan et al., *Planta* 165, 322 (1985).

Spontaneous variation has been observed among the regenerates. The variation is often termed somoclonal variation. Plant geneticists have been able to extract corn regenerates with agronomically desirable traits from the somoclonal varieties. Cowley et al., *Agro. Abst.* 1984:60; Gracen et al., *Agro. Abst.* 1984:68; and Lee et al., *Agro. Abst.* 1984:76. These regenerates have been used in corn breeding programs. In each instance, the regenerates were all obtained from embryogenic and organogenic calli derived from immature embryos, generally 10-15 days post-pollination.

Embryogenic and organogenic calli can be induced from a variety of corn plant tissues, in addition to immature embryos as described above. These plant tissues include anthers (Ting et al., *Plant Sci. Lett.* 23, 139 (1981)), glumes (Suprasenna et al., *Theor. Appl. Genet.* 72, 120 (1986)), leaf bases (Chang, *Plant Cell Rep.* 2, 183 (1983)), mesocotyls (Harms et al., *Z. Pflangenzuchtg* 77, 347 (1976)), seedling segments (Santos et al., *Plant Sci. Letts.* 33, 309 (1984)), immature ears (Molnar et al., *Maize Genet. Corp. News Lett.*, 54, 52 (1980)), and immature tassels (Rhodes et al., *Maize Genet. Corp. News Lett.* 56, 148 (1982)). Regeneration of plants from these corn tissues, except immature embryos, has been inefficient. Immature embryo callus is very efficient for regeneration. All of these explant tissues are obtained from living plants, which is a disadvantage in that time and space are necessary to grow corn plants to obtain the desired tissue.

This disadvantage is overcome by the present invention, which utilizes the mature corn embryo as the explant tissue for the production of embryogenic and organogenic calli. Corn plants are regenerated from this calli. Use of dried mature embryos for corn regeneration is superior to other explant tissues since (a) it is not necessary to grow plants, and (b) callus can be induced from the mature embryo in about a week.

SUMMARY OF THE INVENTION

The present invention is directed to a process for regenerating plants from mature corn embryos. The process comprises the steps of culturing the mature embryo on a callus induction medium to induce callus, subculturing the callus on a maintenance medium to maintain the callus, and subculturing the maintained callus on a regeneration medium to produce plants.

Most genotypes of corn can be regenerated using this procedure, even when 2,4-D is utilized as the hormone. This is the first instance that most genotypes have been regenerable on a tissue culture medium containing 2,4-D. The callus may be maintained for prolonged periods of time on the maintenance medium.

DETAILED DESCRIPTION OF THE INVENTION

The present invention is directed to a process for regenerating corn, *Zea mays*, through the use of cell or tissue culture from a mature embryo. In this process, regenerated plants are obtained which can be placed in soil and grown to maturation. In general, the process comprises (a) culturing a mature corn embryo on a medium to produce callus, (b) culturing the callus on a medium to maintain the callus, (c) culturing the callus on a medium to regenerate plants.

The plant tissue which is utilized in the process is the mature embryo. The mature embryo is isolated from the kernel after the kernel has been softened by soaking in water or by lying in contact with medium overnight (10–16 hours). The radical section is removed from the softened kernel. The remaining plumule section is cut in half and placed cut-surface down on the callus induction medium.

The callus induction medium comprises mineral salts, vitamins and sucrose. The mineral salts comprise macroelements and microelements. The macroelements used in the induction medium may be the following compounds: magnesium sulfate, calcium chloride, monopotassium phosphate, potassium nitrate and ammonium nitrate. The microelements contained in this medium are: boric acid, manganese sulfate, zinc sulfate, sodium molybdate (VI), copper (II) sulfate, cobalt choride, potassium iodide, iron (II) sulfate and disodiumethylenediamine tetraacetic acid (EDTA). This combination of mineral salts is known in the art as the MS mineral salts. Other combinations of mineral salts may also be used as long as they do not adversely affect callus induction. Many combinations of mineral salts are known. These include, but are not limited to, N6, Heller, Nitsch and Nitsch, B5 and White.

The preferred amounts of the macroelements and microelements which are used to prepare one liter of medium are: 370 mg magnesium sulfate heptahydrate, 440 mg calcium chloride dihydrate, 170 mg monopotassium phosphate, 1900 mg potassium nitrate, 1650 mg ammonium nitrate, 6.2 mg boric acid, 16.9 mg manganese sulfate monohydrate, 8.6 mg zinc sulfate heptahydrate, 0.25 mg sodium molybdate (VI) dihydrate, 0.025 mg copper (II) sulfate pentahydrate, 0.025 mg cobalt chloride hexahydrate, 0.83 mg potassium iodide, 27.8 mg iron (II) sulfate heptahydrate, and 37.3 mg disodium-EDTA.

The callus induction medium further contains vitamins. The vitamins utilized are myo-inositol and thiamine. The preferred amounts of the vitamins used to prepare one liter of medium are 0.8 mg thiamine hydrochloride and 100 mg myo-inositol.

The callus induction medium contains 1–10%, preferably 2%, sucrose, and a gelling agent such as agar or Gelrite$^{TM}$ (Kelco Commercial Development, Post Office Box 23076, San Diego, Calif. It is preferred to use Gelrite at a concentration of 0.2%. The medium has a pH of 5.5–5.8 with a preferred pH of 5.8, and is sterilized by autoclaving.

The medium useful for softening the kernal is the medium described above containing 2% sucrose. It is preferred to use this medium to soften the kernel, rather than soaking the kernel to provide for the detection of contaminants. The kernel is placed embryo-side down on the medium for 10–16 hours.

In addition to the above components, the callus induction medium also contains a hormone. As used herein, "hormone" is intended to mean any natural or synthetic compound which has a regulatory effect on plants or plant tissues and any additive which may be combined with said compound. Plant hormones include auxins and cytokinins. It has been found that the hormone which is useful for callus induction may be selected from the group consisting of (A) 2,4-D; (B) dicamba; (C) chloramben; (D) a mixture of 2,4-D, NAA, indoleacetic acid (IAA) and zeatin; (E) a mixture of dicamba, NAA, IAA and zeatin; (F) a mixture of chloramben, NAA, IAA and zeatin; (G) a mixture of dicamba and 2,4-D; and (H) a mixture of chloramben and 2,4-D.

The amount of hormone present is sufficient to ensure callus formation. generally (A), 1–4 mg/l 2,4-D; (B) 1–5 mg/l decamba; (C) 1–5 mg/l chloramben; (D) 2–3 mg/l 2,4-D, 5–20 μM NAA, 5–20 μM IAA and 5–20 μM zeatin; (E) 2–3 mg/l dicamba, 5–20 μM NAA, 5–20 μM IAA and 5–20 μM zeatin; (F) 2–3 mg/l chloramben, 5–20 μM NAA, 5–20 μM IAA and 5–20 μM zeatin; (G) 2–3 mg/l of a mixture of dicamba and 2,4-D in a weight ratio of about 10–15:1 and (H) 2–3 mg/l of a mixture of chloramben and 2,4-D in a weight ratio of about 10–15:1 are utilized as the hormone in the callus induction medium. It is preferred to use 2 mg/l 2,4-D; (B) 2 mg/l dicamba; (C) 3 mg/l chloramben; (D) 2 mg/l 2,4-D, 10 μM NAA, 10 μM IAA and 10 μM zeatin; (E) 2 mg/l dicamba, 10 μM NAA, 10 μM IAA and 10 μM zeatin; (F) 2 mg/l chloramben, 10 μM NAA, 10 μM IAA and 10 μM zeatin; (G) 2 mg/l of a mixture of dicamba and 2,4-D in a weight ratio of about 10–15:1; and (H) 2 mg/l of a mixture of chloramben and 2,4-D in a weight ratio of about 10–15:1.

The plant tissue is plated on the callus induction medium and cultured in the dark at 24°–30° C., preferably 28° C., for 5–10 days, preferably seven days. During this time, the embryo undergoes dedifferentiation and callus formation. After culturing on the callus induction medium, the callus is transferred and subcultured on a maintenance medium. The callus is cultured on the maintenance medium as long as desired with transfers to fresh medium occurring every 10–14 days. Callus has been maintained for more than 18 months without losing its regeneration capability. The culturing on the maintenance medium is performed in the dark at 24°–30° C., preferably 28° C.

The maintenance medium comprises mineral salts, vitamins, amino acids, sucrose and a hormone. The mineral salts and vitamins are the same as described for the callus induction medium. 1–3%, preferably 2%, sucrose is utilized. The medium preferably contains Gelrite at about 0.2% and has a pH of 5.5–6.0, with pH 5.8 preferred. The maintenance medium also contains amino acids. The amino acids utilized are L-proline and casamino acids. 5–50 mM L-proline and 100–500 mg/l casamino acids are used. The preferred amounts are 10 mM L-proline and 100 mg/l casamino acids. The maintenance medium also contains a hormone which may be (A) 2,4-D; (B) dicamba; (C) chloramben; (D) a mixture of dicamba and 2,4-D; or (E) a mixture of chloramben and 2,4-D. Generally, (A) 1–3 mg/l 2,4-D; (B) 1–4 mg/l dicamba; (C) 1–4 mg/l chloramben; (D) 1–3 mg/l of a mixture of dicamba and 2,4-D in a weight ratio of about 10–15:1; or (E) 1–3 mg/l of a mixture of chloramben and 2,4-D in a weight ratio of about 10–15:1 are utilized in the maintenance medium. The preferred amounts are (A) 2 mg/l 2,4-D; (B) 2 mg/l dicamba; (C) 3 mg/l chloramben; (D) 2 mg/l of a mixture of dicamba and 2,4-D in a weight ratio of about 10–15:1; and (E) 2 mg/l of a mixture of chloramben and 2,4-D in a weight ratio of about 10–15:1.

After culturing the callus on the maintenance medium for the desired time period, the callus is transferred and subcultured on a regeneration medium. The regeneration medium comprises mineral salts, vitamins and sucrose. The mineral salts and vitamins are the same as the callus induction medium. 1–3%, preferably 2%, sucrose is utilized in this medium. The regeneration medium preferably contains Gelrite at about 0.2% and has a pH of 5.5–6.0, with pH 5.8 preferred. Culturing on the regeneration medium is performed at 24°–30° C., preferably 28° C., with a 16 hour diffused light/8 hour dark cycle. Plantlets are transferred to culture tubes containing fresh regeneration medium when they reach 1–3 cm in size, for further development. When the plantlets reach 10–15 cm in size, they are transferred to soil and grown in the greenhouse.

Alternatively, the callus after maintenance is first transferred and subcultured on a pre-regeneration medium before transfer and subculture on the regeneration medium. Culturing on the pre-regeneration medium is performed for 10–20 days at 24°–30° C., preferably 28° C., with a 16 hour diffused light/8 hour dark cycle before transfer to the regeneration medium. The pre-regeneration medium comprise mineral salts, vitamins, amino acids, sucrose and a hormone. This medium is the same as the maintenance medium, except that the concentration of the hormone is reduced. Generally, the hormone concentration is 0.05–0.5 $\mu$M, preferably 0.1 $\mu$M.

The process is useful for regenerating plants from the mature embryo of many cultivars of corn using 2,4-D. Other hormones can also be utilized in addition to 2,4-D, as described herein. The present invention process is capable of regenerating cultivars of corn using medium with 2,4-D which were previously incapable of regeneration with 2,4-D-containing medium according to prior art processes. Examples of these cultivars include B73, A632 and Mo17.

The present invention will be further described by reference to the following non-limiting examples. All of the corn cultivars used herein are publicly available.

EXAMPLE 1

Preparation of Solutions

The following stock solutions were prepared for use in making the media described in further detail below.

1. Hormones (A) 1 mg/ml stock solutions of 2,4-D, dicamba or chloramben were prepared by dissolving 50 mg of the hormone in 50 ml of sterile water.

(B) 5 mM stock solutions of NAA, IAA or zeatin were prepared by dissolving 46.55 mg of NAA, 41.25 mg of IAA or 54.75 mg of zeatin in 50 ml of sterile water.

EXAMPLE 2

Preparation of Media

1. Callus Induction Medium

The callus induction medium was prepared by dissolving one packet of Murashige minimal organics medium without sucrose, but which contained a pH buffering agent (Gibco Laboratories Catalog No. 510-3118), 20 g of sucrose, 0.4 mg of thiamine hydrochloride and 2 ml of the 2,4-D stock solution in 800 ml of sterile water. A small amount of water was used to rinse out the packet. 2 g of Gelrite was added and the volume was brought to one liter with sterile water. The medium was sterilized by autoclaving and poured into petri dishes. Media containing other hormones were prepared analogously using the appropriate amounts of the hormone stock solutions.

2. Maintenance Medium

Maintenance medium was prepared as described above except that the appropriate amounts of the hormone stock solutions were utilized and that 100 mg of casamino acids and 1.15 mg of L-proline were initially dissolved.

3. Pre-Regeneration Medium

Pre-regeneration medium was prepared as described above for maintenance medium except that the appropriate amounts of the hormone stock solutions were utilized.

4. Regeneration Medium

Regeneration medium was prepared as described above for maintenance medium except that hormones were not included and the medium was poured into either petri dishes or culture tubes.

5. Kernel Softening Medium

Kernel softening medium was prepared as described above for callus induction medium except that hormones were not included.

EXAMPLE 3

Isolation of Mature Embryos for Callus Formation

Kernels of the corn *Zea mays* L. were surface-sterilized for 25 minutes in a 0.25% sodium hypochlorite solution containing 0.01% (w/v) of the detergent SDS. The kernels were then washed five times with sterile water over a period of one hour. The kernels were softened by soaking in sterile water overnight (10–16 hours). The embryo of each kernel was removed by dissection and the isolated embryo was cut transversely between the plumule and radicle. The radicle sections were discarded and the plumule sections were longitudinally sliced into halves.

Alternatively, the isolation was performed in the same manner, except that the kernels were softened by placing the kernel embryo-side down on solid medium containing 2% sucrose and culturing overnight (10–16 hours) or until the endosperm and embryo tissue became softened.

EXAMPLE 4

Corn Regeneration

Mature embryo halves prepared as described in Example 3 from Zea mays L. B73 were plated cut-surface down on callus induction medium containing 2 mg/ml 2,4-D, contained in a petri dish. The petri dish was placed in the dark at 28° C. and cultured for six days. At that time, each callus was transferred to maintenance medium containing 2 mg/ml 2,4-D, contained in a petri dish. The petri dish was placed in the dark at 28° C. and cultured for 60 days, with transfers to fresh maintenance medium occurring every 10–14 days. The callus was then transferred to regeneration medium, contained in a petri dish, and cultured in the light at 28° C. with a 16 hour photoperiod, until the regenerated plantlets were 1–3 cm in size. The plantlets were then transferred to culture tubes (25 mm ×150 mm) containing 10 ml of fresh regeneration medium and cultured in the light until they were 10–15 cm in size. At that point, the plantlets were transferred to soil and grown to maturity in a greenhouse.

In accordance with the above procedure, the callus was cultured on maintenance medium for up to 18 months with transfers to fresh medium every 10–14 days. Plants were then regenerated as described above.

EXAMPLE 5

Corn Regeneration

Mature embryo halves prepared as described in Example 3 from *Zea mays* L. A632 and Mo17 were cultured as described in Example 4. Plants were regenerated for each cultivar and grown to maturity in a greenhouse.

EXAMPLES 6-11

Corn Regeneration

In accordance with Examples 3-5, mature embryo halves were isolated from *Zea mays* L. B73, A632 and Mo17, and cultured on the media containing the indicated hormones. Plants were obtained after transfer to regeneration medium in accordance with these examples.

| Example | Callus Induction Medium | Maintenance Medium |
|---|---|---|
| 6 | 2 mg/l dicamba | 2 mg/l dicamba |
| 7 | 3 mg/l chloramben | 3 mg/l chloramben |
| 8 | 2 mg/l 2,4-D, 10 μM NAA, 10 μM IAA and 10 μM zeatin | 2 mg/l 2,4-D |
| 9 | 2 mg/l dicamba, 10 μM NAA, 10 μM IAA and 10 μM zeatin | 2 mg/l dicamba |
| 10 | 2 mg/l 2,4-D | 2 mg/l dicamba |
| 11 | 1.5 mg/l dicamba and 0.10 mg/l 2,4-D | 2 mg/l dicamba |

EXAMPLE 12

Corn Regeneration

The procedure described in Examples 4-11 was followed except that prior to culturing on the regeneration medium, the maintained callus was cultured on pre-regeneration medium containing 0.1 μM of the hormone used in the maintenance medium, contained in a petri dish, at 28° C. in the light for 10-20 days. Plants were regenerated and matured in a greenhouse.

While the invention has been described in connection with specific embodiments thereof, it will be understood that it is capable of further modifications. This application is intended to cover any variations, uses or adaptations of the invention following, in general, the principles of the invention and including such departures from the present disclosures as come within known and customary practice within the art to which the invention pertains.

What is claimed is:

1. A process for regenerating corn plants from cell or tissue culture which comprises the steps of:
    (a) culturing tissue obtained from a mature corn embryo on a callus induction medium comprising mineral salts, vitamins, sucrose, and a hormone selected from the group consisting of (A) 2,4-dichlorophenoxyacetic acid (2,4-D); (B) dicamba, (C) chloramben, (D) a mixture of 2,4-D, α-naphthalene acetic acid (NAA), indole acetic acid (IAA) and zeatin, (E) a mixture of dicamba, NAA, IAA, and zeatin. (F) a mixture of chloramben, NAA, IAA and zeatin, (G) a mixture of dicamba and 2,4-D, and (H) a mixture of chloramben and 2,4-D in the dark at 24°-30° C. for callus formation;
    (b) subculturing said callus on a maintenance medium comprising mineral salts, vitamins, sucrose, L-proline, casamino acids and a hormone selected from the group consisting of (A) 2,4-D, (B) dicamba, (C) chloramben, (D) a mixture of dicamba and 2,4-D, and (E) a mixture of chloramben and 2,4-D in the dark at 24°-30° C. for callus maintenance; and
    (c) subculturing said callus on a regeneration medium comprising mineral salts, vitamins and sucrose in the light at 24°-30° C. for plant formation.

2. The process of claim 1 wherein said callus is subcultured on a pre-regeneration medium prior to subculturing on the regeneration medium, wherein the pre-regeneration medium comprises mineral salts, vitamins, sucrose, L-proline, casamino acids and a hormone selected from the group consisting of (A) 2,4-D, (B) dicamba, (C) chloramben, (D) a mixture of dicamba and 2,4-D, and (E) a mixture of chloramben and 2,4-D in an amount from about 0.05 μM to about 0.5 μM in the light at 24°-30° C.

3. The process of claim 1 wherein the concentrations of said hormones of said media are:
    (1) (A) 1-4 mg/l 2,4-D, (B) 1-5 mg/l dicamba, (C) 1-5 mg/l chloramben, (D) 2-3 mg/l 2,4-D, 5-20 μM NAA, 5-20 μM IAA and 5-20 μM zeatin. (E) 2-3 mg/l dicamba, 5-20 μM NAA, 5-20 μM IAA and 5-20 μM zeatin, (F) 2-3 mg/l chloramben, 5-20 μM NAA, 5∝20 μM IAA and 5-20 μM zeatin, (G) 2-3 mg/l of a mixture of dicamba and 2,4-D in a weight ratio of about 10-15:1, or (H) 2-3 mg/l of a mixture of chloramben and 2,4-D in a weight ratio of about 10-15:1 in the callus induction medium; and
    (2) (A) 1-3 mg/l 2,4-D, (B) 1-4 mg/l dicamba, (C) 1-4 mg/l chloramben, (D) 1-3 mg/l of a mixture of dicamba and 2,4-D in a weight ratio of about 10-15:1, or (E) 1-3 mg/l of a mixture of chloramben and 2,4-D in a weight ratio of about 10-15:1 in the maintenance medium.

4. The process of claim 2 wherein the concentrations of said hormones in said media are:
    (1) (A) 1-4 mg/l 2,4-D, (B) 1-5 mg/l dicamba, (C) 1-5 mg/l chloramben, (D) 2-3 mg/l 2,4-D, 5-20 μM NAA, 5-20 μM IAA and 5-20 μM zeatin, (E) 2 mg/l dicamba, 5-20 μM NAA, 5-20 μM IAA and 5-20 μM zeatin in the callus induction medium; and
    (2) (A) 1-3 mg/l 2,4-D, (B) 1-4 mg/l dicamba, (C) 1-4 mg/l chloramben, (D) 1-3 mg/l of a mixture of dicamba and 2,4-D in a weight ratio of about 10-15:1, or (E) 1-3 mg/l of a mixture of chloramben and 2,4-D in a weight ratio of about 10-15:1 in the maintenance medium.

5. The process of claim 3 wherein the concentrations of said hormones in said media are:
    (1) (A) 2 mg/l 2,4-D, (B) 2 mg/l dicamba, (C) 3 mg/l chloramben, (D) 2 mg/l 2,4-D, 10 μM NAA, 10 μM IAA and 10 μM zeatin, (E) 2 mg/l dicamba, 10 μM NAA, 10 μM IAA and 10 μM zeatin, (F) 2 mg/l chloramben, 10 μM NAA, 10 μM IAA and 10 μM zeatin, (G) 2 mg/l of a mixture of dicamba and 2,4-D, or (H) 2 mg/l of a mixture of chloramben and 2,4-D in a weight ratio of 10-15:1 in said callus induction medium; and
    (2) (A) 2 mg/l 2,4-D, (B) 2 mg/l dicamba, (C) 3 mg/l chloramben, (D) 2 mg/l of a mixture of dicamba and 2,4-D in a weight ratio of 10-15:1, or (E) 2 mg/l of a mixture of chloramben and 2,4-D in a weight ratio of 10-15:1 in said maintenance medium.

6. The process of claim 4 wherein the concentrations of said hormones in said media are:

(1) (A) 2 mg/l 2,4-D, (B) 2 mg/l dicamba, (C) 3 mg/l chloramben, (D) 2 mg/l 2,4-D, 10 μM NAA, 10 μM IAA and 10 μM zeatin, (E) 2 mg/l dicamba, 10 μM NAA, 10 μM IAA and 10 μM zeatin, (F) 2 mg/l chloramben, 10μM NAA, 10 μM IAA and 10 μM zeatin, (G) 2 mg/l of a mixture of dicamba and 2,4-D, or (H) 2 mg/l of a mixture of chloramben and 2,4-D in a weight ratio of 10-15:1 in said callus induction medium; and (2) (A) 2 mg/l 2,4-D, (B) 2 mg/l dicamba, (C) 3 mg/l chloramben, (D) 2 mg/l of a mixture of dicamba and 2,4-D in a weight ratio of 10-15:1, or (E) 2 mg/l of a mixture of chloramben and 2,4-D in a weight ratio of 10-15:1 in said maintenance medium.

7. The process of claim 1 wherein the concentration of L-proline is 5-50 mM and the concentration of casamino acids is 100-500 mg/l.

8. The process of claim 2 wherein the concentration of L-proline is 5-50 mM and the concentration of casamino acids is 100 ∝ 500 mg/l.

9. The process of claim 1 wherein the sucrose concentrations in said media are:
(1) 2-10% in said callus induction medium;
(2) 1-3% in said maintenance medium; and
(3) 1-3% in said generation medium;

10. The process of claim 2 wherein the sucrose concentrations in said media are:
(1) 2-10% in said callus induction medium;
(2) 1-3% in said maintenance medium;
(3) 1-3% in said regeneration medium; and
(4) 1-3% in said pre-regeneration medium.

11. A process for regenerating corn plants from cell or tissue culture which comprises the steps of:

(a) culturing tissue obtained from a mature corn embryo on a callus induction medium comprising mineral salts, vitamins, sucrose and a hormone selected from the group consisting of (A) 1-4 mg/l 2,4-dichlorophenoxyacetic acid (2,4-D), (B) 1-5 mg/l dicamba, (C) 1-5 mg/l chloramben, (D) 2-3 mg/l 2,4-D, 5-20 μM α-naphthalene acetic acid (NAA), 5-20 μM α-indole acetic acid (IAA) and 5-20 μM zeatin, (E) 2-3 mg/l dicamba, 5-20 μM NAA, 5-20 μM IAA and 5-20 μM zeatin, (F) 2-3 mg/l chloramben, 5-20 μM NAA, 5-20 μM IAA and 5-20 μM zeatin, (G) 2-3 mg/l of a mixture of dicamba nd 2,4-D in a weight ratio of about 10-15:1, or (H) 2-3 mg/l of a mixture of chloramben and 2,4-D in a weight ratio of about 10-15:1 in the dark at 24°-30° C. for callus formation;

(b) subculturing said callus on a maintenance medium comprising mineral salts, vitamins, sucrose, 10-50 mM L-proline, 100-500 mg/l casamino acids and a hormone selected from the group consisting of (A) 1-3 mg/l 2,4-D, (B) 1-4 mg/l dicamba, (C) 1-4 mg/l chloramben, (D) 1-3 mg/l of a mixture of dicamba and 2,4-D in a weight ratio of about 10-15:1, or (E) 1-3 mg/l of a mixture of chloramben and 2,4-D in a weight ratio of about 10-15:1 in the dark at 24°-30° C. for callus maintenance; and (c) subculturing said callus on a regeneration medium comprising mineral salts, vitamins and sucrose in the light at 24°-30° C. for plant formation.

12. The process of claim 11 wherein said callus is subcultured on a pre-regeneration medium prior to subculturing on the regeneration medium, wherein the pre-regeneration medium comprises mineral salts, vitamins, sucrose, 5-50 mM L-proline, 100-500 mg/l casamino acids and a hormone selected from the group consisting of (A) 2,4-D, (B) dicamba, (C) chloramben, (D) a mixture of dicamba and 2,4-D and mixtures thereof in an amount from about 0.05 μM to about 0.1 μM in the light at 24°-30° C.

13. The process of claim 11 wherein the concentrations of said hormones in said media are:

(1) (A) 2 mg/l 2,4-D, (B) 2 mg/l dicamba, (C) 3 mg/l chloramben, (D) 2 mg/l 2,4-D, 10 μM NAA, 10 μM IAA and 10 μM zeatin, (E) 2 mg/l dicamba, 10 μM NAA, 10 μM IAA and 10 μM zeatin, (F) 2 mg/l chloramben, 10 μM NAA, 10 μM IAA and 10 μM zeatin, (G) 2 mg/l of a mixture of dicamba and 2,4-D, or (H) 2 mg/l of a mixture of chloramben and 2,4-D in a weight ratio of 10-15:1 in said callus induction medium; and (2) (A) 2 mg/l 2,4-D, (B) 2 mg/l dicamba, (C) 3 mg/l chloramben, (D) 2 mg/l of a mixture of dicamba and 2,4-D in a weight ratio of 10-15:1, or (E) 2 mg/l of a mixture of chloramben and 2,4-D in a weight ratio of 10-15:1 in said maintenance medium.

14. The process of claim 12 wherein the concentrations of said hormones in said media are:

(1) (A) 2 mg/l 2,4-D, (B) 2 mg/l dicamba, (C) 3 mg/l chloramben, (D) 2 mg/l 2,4-D, 10 μM NAA, 10 μM IAA and 10 μM zeatin, (E) 2 mg/l dicamba, 10 μM NAA, 10 μM IAA and 10 μM zeatin, (F) 2 mg/l chloramben, 10 μM NAA, 10 μM IAA and 10 μM zeatin, (G) 2 mg/l of a mixture of dicamba and 2,4-D, or (H) 2 mg/l of a mixture of chloramben and 2,4-D in a weight ratio of 10-15:1 in said callus induction medium; and (2) (A) 2 mg/l 2,4-D, (B) 2 mg/l dicamba, (C) 3 mg/l chloramben, (D) 2 mg/l of a mixture of dicamba and 2,4-D in a weight ratio of 10-15:1, or (E) 2 mg/l of a mixture of chloramben and 2,4-D in a weight ratio of 10-15:1 in said maintenance medium.

15. The process of claim 11 wherein the sucrose concentrations in said media are:
(1) 2-10% in said callus induction medium;
(2) 1-3% in said maintenance medium; and
(3) 1-3% in said regeneration medium.

16. The process of claim 12 wherein the sucrose concentrations in said media are:
(1) 2-10% in said callus induction medium;
(2) 1-3% in said maintenance medium;
(3) 1-3% in said regeneration medium; and
(4) 1-3% in said pre-regeneration medium.

17. The process of claim 13 wherein the sucrose concentrations in said media are:
(1) 2-10% in said callus induction medium;
(2) 1-3% in said maintenance medium; and
(3) 1-3% in said regeneration medium.

18. The process of claim 14 wherein the sucrose concentrations in said media are:
(1) 2-10% in said callus induction medium;
(2) 1-3% in said maintenance medium;
(3) 1-3% in said regeneration medium; and
(4) 1-3% in said pre-regeneration medium.

* * * * *